US006686998B2

(12) United States Patent
Gianchandani et al.

(10) Patent No.: US 6,686,998 B2
(45) Date of Patent: Feb. 3, 2004

(54) METHOD AND APPARATUS FOR GLOW DISCHARGES WITH LIQUID MICROELECTRODES

(75) Inventors: Yogesh B. Gianchandani, Madison, WI (US); Chester G. Wilson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 185 days.

(21) Appl. No.: 09/997,799

(22) Filed: Nov. 30, 2001

(65) Prior Publication Data

US 2003/0103205 A1 Jun. 5, 2003

(51) Int. Cl.[7] .................................................. G01J 3/30
(52) U.S. Cl. ........................ 356/316; 356/311; 313/163
(58) Field of Search ................................ 356/311, 316, 356/313; 313/163, 165, 172, 170, 619, 622, 631

(56) References Cited

U.S. PATENT DOCUMENTS

| | | | | |
|---|---|---|---|---|
| 3,809,479 A | * | 5/1974 | Whelan et al. ............. | 356/314 |
| 4,630,924 A | * | 12/1986 | Meyer ........................ | 356/316 |
| 5,122,713 A | * | 6/1992 | Liang et al. ............ | 315/111.21 |
| 5,728,253 A | * | 3/1998 | Saito et al. ............ | 156/345.25 |

OTHER PUBLICATIONS

T. Cserfalvi, et al., "Emission Studies on a Glow Discharge in Atmospheric Pressure Air Using Water as a Cathode," J. Phys. D.: Appl. Phys., vol. 26, 1993, pp. 2184–2188.

R. Kenneth Marcus, et al., "An Atmospheric Pressure Glow Discharge Optical Emission Source for the Direct Sampling of Liquid Media," Analytical Chemistry, vol. 73, No. 13, Jul. 1, 2001, pp. 2903–2910.

Gareth Jenkins, et al., "Optical Emission Detection of Liquid Analytes Using a Micro–Machined D.C. Glow–Discharge Device at Atmospheric Pressure," Micro Total Analysis Systems, 2001, J.M. Ramsey and A. van den Berg (eds.), Kluwer Academic Publishers, The Netherlands, Oct., 2001, pp. 349–350.

* cited by examiner

Primary Examiner—Frank G. Font
Assistant Examiner—Layla Lauchman
(74) Attorney, Agent, or Firm—Foley & Lardner

(57) ABSTRACT

Glow discharge apparatus having liquid electrodes includes a substrate with a top surface on which cathode and anode electrodes are formed. The cathode electrode may be formed with a cathode terminal port formed to hold a liquid which is spaced from the anode electrode by an inter-electrode surface of the substrate. Electrical conductors are connected to the anode and cathode electrodes to allow a voltage to be applied between them, resulting in a glow discharge in the gap over the inter-electrode surface that causes sputtering of the liquid in the cathode terminal port into the glow discharge. Excitation by the glow discharge of the sputtered or evaporated liquid allows spectroscopic analysis of the constituents of the liquid in the electrode.

51 Claims, 6 Drawing Sheets

METHOD AND APPARATUS FOR GLOW DISCHARGES WITH LIQUID MICROELECTRODES

This invention was made with United States government support awarded by the following agency: NSF Grant No: 9985422. The United States has certain rights in this invention.

FIELD OF THE INVENTION

This invention pertains generally to the field of microelectromechanical systems, microplasmas and particularly glow discharges, and to spectroscopy using glow discharges.

BACKGROUND OF THE INVENTION

Because of the risk of industrial and biochemical pollution of potable water sources, diagnostic tools and systems that can provide rapid on-site tests for contaminants are of increasing importance. At present, water quality assessment is a relatively elaborate process, requiring sample transportation to centralized locations at which laboratory analysis is conducted. This analysis is typically done with a plasma spectrometer, a machine which varies in size from tabletop models to room size systems. In a plasma spectrometer, the water sample is sprayed into a high frequency radio frequency (RF) inductively coupled plasma, and atomic transitions of the impurities are analyzed to determine the composition and quantity of the water impurities. This process is similar to the detection of gases in plasmas.

In addition to plasma spectrometry, various other techniques are available for the diagnosis of gas and water impurities, several of which have been miniaturized using microelectromechanical systems (MEMS) technology. One example is mass spectrometry which measures the ratio of ion mass to charge for gases using various techniques. Quadrupole mass spectrometers have an ion source, a quadrupole electrostatic lens to focus the ion flow, and an array of detectors. Ions with smaller mass to charge ratios are electrostatically deflected more than larger mass ions. A micromachined quadrupole mass spectrometer has been constructed with 500 micron diameter quadrupole electrodes. Time of flight mass spectrometers ionize gas atoms quickly, accelerate the ions, typically electrostatically, and measure their time of flight, which is a function of ion mass. Ion mobility mass spectrometers have the capability of operating at atmospheric pressure. These devices ionize gas using DC or RF voltage, or lasers. Separation of species is based on their different mobilities in a background gas. Such RF-based ion mobility spectrometers have also been miniaturized. Gas chromatographs separate different gases in a carrier gas flowing through a heated tube by exploiting differences in mobility for analysis. Detection mechanisms for chromatography vary, with gas ionization and spectral analysis being common. Efforts have also been made to miniaturize such gas chromatographs.

Microplasmas have been the subject of increased research in recent years. For example, DC microplasmas for silicon etching have been ignited between thin-film metal electrode features patterned on the substrate to be etched, C. G. Wilson, Y. B. Gianchandani, "Silicon Micromachining Using In-Situ DC Microplasmas," JMEMS, Vol. 10, No. 1, March, 2001, pp. 50–54. Efforts have been directed at miniaturizing inductively coupled plasmas for gas spectroscopy, J. A. Hopwood, "A Microfabricated Inductively Coupled Plasma Generator," JMEMS, Vol. 9, No. 3, September, 2000, pp. 309–313, and to utilize DC microplasmas as an optical emission source for gas chromatography, J. C. T. Eijkel, H. Stoeri, A. Manz, "A DC Microplasma on a Chip Employed as an Optical Emission Detector for Gas Chromatography," Anal. Chem., Vol. 72, June, 2000, pp. 2547–2552. Atomic transitions of metallic impurities are typically best detected from spectroscopic analysis of DC plasma emissions. See, N. W. Routh, "DCP Advantages," Applied Research Laboratories Application Reports. Efforts have also been made to employ a water sample as a cathode, with a metallic anode for spectroscopic use. T. Cserfalvi, P. Mezei, "Emission Studies on a Glow-Discharge in Atmospheric Air Using Water as a Cathode," J. Phys. D (Appl. Phys.), Vol. 26, 1993, pp. 2184–2188; R. K. Marcus, W. C. Davis, "An Atmospheric Pressure Glow Discharge Optical Emission Source for the Direct Sampling of Liquid Media," Anal. Chem., Vol. 73, 2000, pp. 2903–2910. Such systems have also been implemented in a MEMS device. G. Jenkins, A. Manz, "Optical Emission Detection of Liquid Analytes Using a Micro-Machined DC Glow Discharge Device at Atmospheric Pressure," $\mu$TAS, October, 2001, pp. 349–350.

SUMMARY OF THE INVENTION

The glow discharge apparatus in accordance with the invention utilizes liquid electrodes which allow spectrometric analysis of liquid samples and particularly water samples for determining contaminants in the water. The invention may also be utilized as a micro light source that provides light output at visible or non-visible wavelengths that can be selected by selection of the liquid utilized in the electrodes or of the materials dissolved or suspended in the electrode liquids.

The glow discharge apparatus in accordance with the invention includes a substrate with a top surface and a cathode electrode and an anode electrode formed thereon. At least the cathode electrode includes a cathode terminal port formed as a depression in the substrate which is formed to hold a liquid sample to be analyzed or otherwise sputtered or evaporated into the glow discharge. The anode electrode also preferably includes an anode terminal port spaced from the cathode terminal port by an inter-electrode gap, with the substrate being electrically insulating between the anode electrode and the cathode electrode. An anode electrical conductor on the substrate is electrically connected to the anode electrode and a cathode electrical conductor on the substrate is electrically connected to the cathode electrode to allow a voltage to be applied from a voltage source between the anode electrode and cathode electrode. The applied voltage creates a glow discharge in the gap over the inter-electrode gap which results in sputtering and/or of the liquid in the cathode terminal port into the gap and its excitation by the discharge in the gap. The spectrum of the light emitted from the discharge will depend on the constituents of the liquid sputtered or evaporated into the gap, allowing spectroscopic analysis of the material of the liquid in the cathode terminal port. The spectrum of the light emitted will also depend on the ambient pressure (which may also be above or below atmospheric pressure if the apparatus is enclosed) and on the power density of the discharge. Spectroscopic analysis can be carried out, for example, by a spectrometer which is coupled to the light in the discharge by an optical fiber or by a microspectrometer formed with the glow discharge apparatus. Alternatively, by choosing the constituents of the liquid in the cathode electrode, the light emitted in the discharge at the gap can be selected to provide a convenient micro light source of selectable wavelengths.

The cathode electrode preferably includes a reservoir formed in the substrate and a channel extending from the reservoir to the cathode terminal port, with an insulating layer covering the channel so that only the terminal port is in electrical communication with the glow discharge in the inter-electrode gap. The anode electrode may be formed in a similar fashion, having a reservoir and a channel extending to the anode terminal port with an insulating covering over the channel. The anode and cathode conductors may be formed on the top surface of the substrate extending from the anode and cathode channels to positions spaced away from the anode and cathode electrodes. Insulating material may be formed on the top surface of the substrate covering the conductors with openings formed therein at which electrical leads may be connected to the anode and cathode conductors. The anode electrode may also be formed as a solid conductor having a terminal portion exposed on the surface of the substrate spaced from the cathode terminal port.

A particular advantage of the invention in spectroscopic analysis of water samples is that the water sample and its impurities are effectively sputtered into the glow discharge during operation, eliminating the need for spraying which has otherwise been necessary for detecting non-volatile contaminants. Moreover, for use in either spectroscopic analysis or as a light source, the invention has the advantage that electrode wear is eliminated since the active portions of both electrodes may be formed of liquids and thus any electrode material evaporated or burned away is effectively replenished by liquid flow from the reservoirs. Furthermore, a continuous glow discharge can be sustained in air at atmospheric pressure, eliminating the need for a vacuum system. The utilization of two liquid electrodes has the additional advantage that spurious contamination by the anode material is avoided.

The apparatus can be operated in a calibration mode, e.g., with the anode filled with pure water (modified to an appropriate pH level) while the cathode can be filled with the water being tested. Operating the device with DC voltage applied with correct polarity (negative voltage on the cathode) which gives spectroscopic readings on impurities in the sample. Operating with reverse polarity will provide a baseline reading of the pure water (or water with known impurities) in the anode. In addition, the device can be operated with a square wave in a "chopping" mode, to provide continuous impurity and baseline readings.

Further objects, features and advantages of the invention will be apparent from the following detailed description when taken in conjunction with the accompanying drawings.

DETAILED DESCRIPTION OF THE INVENTION

Figure 1:
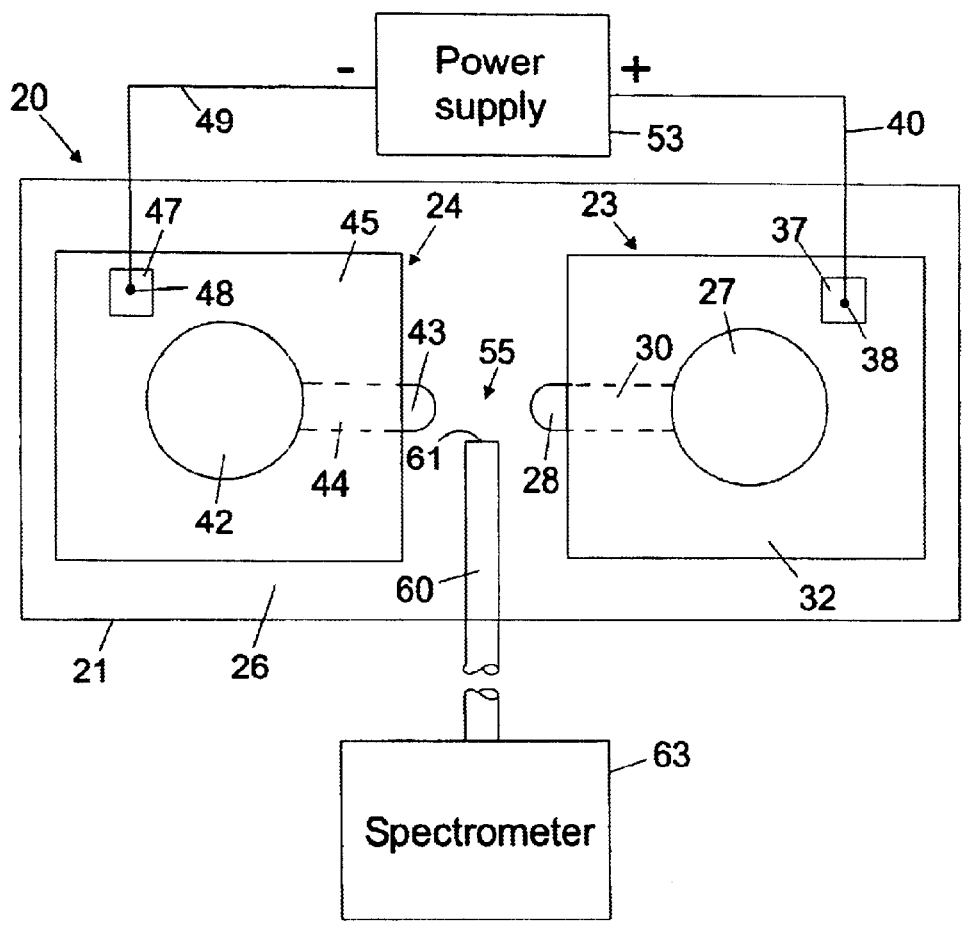
FIG. 1 is a plan view of glow discharge apparatus with liquid electrodes in accordance with the invention.
Figure 2:
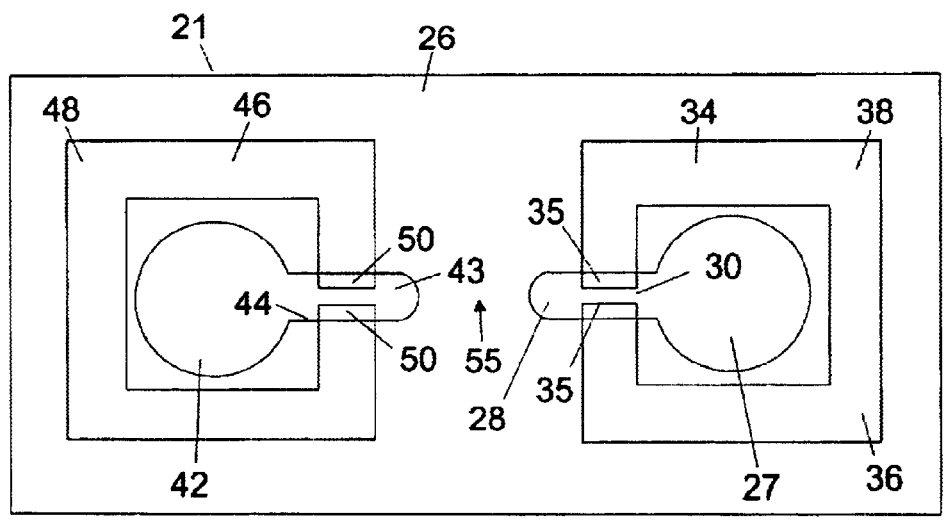
FIG. 2 is a plan view of the substrate with reservoirs, channels and electrode conductors formed thereon for the apparatus of FIG. 1.

With reference to the drawings, apparatus in accordance with the invention for glow discharges using a liquid microelectrode is shown generally at 20 in FIG. 1. The apparatus 20 is particularly well suited for utilization in spectrometry for analysis of liquid samples and particularly water samples for determination of contaminants in the water. The apparatus 20 may also be utilized as a micro light source that provides light output at wavelengths that can be selected by selection of the liquid utilized in the electrodes or the materials dissolved or suspended in the electrode liquids. As illustrated in FIG. 1, the apparatus 20 includes a base substrate 21 which may be formed of various, preferably electrical insulating, materials such as glass. However, other materials may be used as the base substrate, including semiconductors such as silicon, with appropriate doping of the semiconductor or coating of the semiconductor surface to provide appropriate electrical insulation between an anode electrode 23 and a cathode electrode 24. Although a unitary substrate is preferred, the substrate may be formed in multiple parts. The substrate 21 preferably is formed with a flat top surface 26 on which the anode electrode 23 and cathode electrode 24 are formed as discussed further below. The anode electrode 23 includes an anode reservoir 27 preferably formed as a depression in the substrate 21 that extends below the top surface 26 of the substrate, an anode terminal port 28, and a channel 30 (shown in dashed lines in FIG. 1) which extends between the reservoir 27 and the terminal port 28 to transfer liquid from the reservoir 27 to the terminal port 28. The terminal port 28 and the channel 30 are also preferably formed as a depression in the substrate 21 below the top surface 26 of the substrate. A layer of electrical insulation 32 extends over the anode channel 30 and surrounds the anode reservoir 27, also covering electrical conductors 34, shown in FIG. 2 with the cover 32 removed, which extend from terminal positions 35 within the channel 30 outwardly from the channel over the surface of the substrate 26 and are joined behind the reservoir 27 at a section 36. The electrical conducting layer 34 may be formed of a conducting metal which is suited to be in contact with the liquid flowing through the channel 30 at the exposed end sections 35 of the conductor. For example, platinum is relatively resistant to corrosion or electroplating in many solutions that may be utilized in the electrodes. An opening 37 is formed in the conducting layer 32 (e.g., formed of an insulating polymer such as polyimide), to allow access to a portion of the conductor 36 at a position 38 at which a conducting lead 40 may be electrically connected to the conductor 34.

The cathode electrode 24 may be formed in the same manner as the anode electrode, with a cathode reservoir 42, a terminal port 43, a cathode channel 44 extending from the reservoir 42 to the terminal port 43, an insulating layer 45 extending over the channel 44 and covering an electrical conductor 46 (shown in FIG. 2) except at an opening 47 allowing access to the electrical conductor 46 at a position 48 at which a conducting lead 49 is connected to the electrical conductor. The electrical conductor 46 has end sections 50 in the channel 44 which are exposed to the liquid in the channel to make electrical contact therewith.

Figure 3:
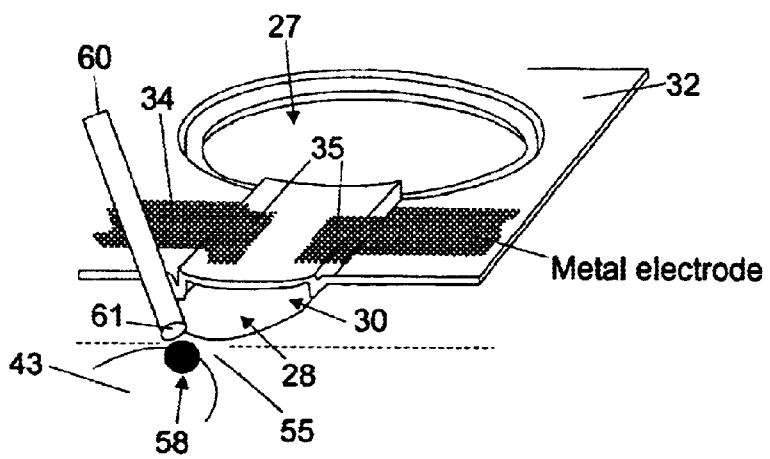
FIG. 3 is a perspective view of a portion of the glow discharge apparatus of the invention.

A power supply 53 is connected to the conducting leads 40 and 49 to apply a voltage between the anode electrode 23 and the cathode electrode 24 to thereby apply a voltage differential between a liquid within the anode reservoir 27, channel 30 and terminal port 28, and a liquid in the cathode reservoir 42, channel 44 and terminal port 43. The power supply is preferably a DC power supply that applies a DC potential between the electrodes, but AC voltage may also be applied as appropriate (e.g., at radio frequencies) to generate the glow discharges. The anode terminal port 28 is separated from the cathode terminal port 43 by an inter-electrode surface 55 which may be a portion of the top surface 26 of the substrate. The application of a positive potential to the liquid in the anode terminal port 28 with respect to the liquid in the cathode terminal port 43 induces a glow discharge plasma in the inter-electrode gap over the inter-electrode surface 55, which causes sputtering of the liquid contained in the cathode terminal port 43. This vaporized liquid is drawn into the inter-electrode gap and is excited by the glow discharge to emit light at characteristic wavelengths based on the constituents in the liquid. This micro discharge, illustrated generally at 58 in the perspective view of FIG. 3, may be utilized to determine the constituents of the liquid in the cathode reservoir. For example, the light from the discharge 58 may be transmitted by an optical fiber 60, which has one end 61 positioned closely adjacent to the micro discharge, and which transmits the light from the discharge to a spectrometer 63 at a remote position. For use in the field, it is preferable that the spectrometer 63 be readily portable. A suitable example is a pager sized spectrometer available from Ocean Optics, USB-2000, which may be connected to a data acquisition computer to store the spectroscopic data. Although a separate spectrometer 63 coupled to the discharge by an optical fiber 60 is shown for illustration, it is understood that a micro spectrometer may be packaged on the substrate 21 directly adjacent to the inter-electrode surface 55. Where the material of the substrate 21 is not hydrophobic, it is preferable that the inter-electrode surface 55 have a hydrophobic coating thereon (e.g., petroleum jelly) so that this surface is not wetted by the liquid (typically, water) that is sputtered from the liquid in the cathode terminal port 43. In the present invention, the inter-electrode gap between the anode terminal port 28 and cathode terminal port 43 is preferably selected to allow a continuous glow discharge at reasonable voltage levels. The spacing of the gap is governed by the breakdown pressure of the discharge, where the ideal spacing is a function of the background pressure, with reasonable minimum dimensions selected such that the electrodes do not short out frequently. Typical spacings between the electrodes are in the range of a few millimeters, preferably 0.5 mm to 10 mm and most preferably four millimeters or less. Exemplary dimensions include terminal ports 28 and 43 having lateral dimensions of 500 $\mu$m×700 $\mu$m, 4.5 mm length of channels 30 and 44, and an inter-electrode spacing between the terminal ports 28 and 43 of, e.g., 2.5 mm.

The apparatus of the invention has several advantages for spectroscopic analysis or for use as a light source. First, for analyzing contaminants in water samples, the water sample and its impurities are effectively sputtered into the glow discharge, eliminating the need for spraying which has otherwise been necessary for detecting non-volatile contaminants. Secondly, electrode wear is eliminated since the active portions of both electrodes may be formed of liquids and the electrodes are effectively replenished by liquid flow from the reservoirs 27 and 42. Third, a continuous glow discharge can be sustained in air at atmospheric pressure, eliminating the need for a vacuum system.

The apparatus can be operated in a calibration mode, e.g., with the anode filled with pure water (modified to an appropriate pH level) while the cathode can be filled with the water being tested. Operating the device with DC voltage applied with correct polarity (negative voltage on the cathode) which gives spectroscopic readings on impurities in the sample. Operating with reverse polarity will provide a baseline reading of the pure water (or water with known impurities) in the anode. In addition, the device can be operated with a square wave in a "chopping" mode, to provide continuous impurity and baseline readings.

Figure 4:
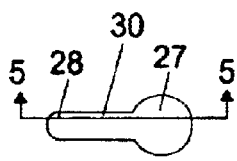
FIG. 4 is a simplified top view of a reservoir and a channel formed in the substrate of the apparatus of FIG. 1.
Figure 5:
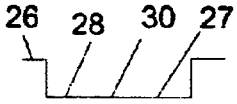
FIG. 5 is a cross-sectional view taken generally along the lines 5—5 of FIG. 4.
Figure 6:
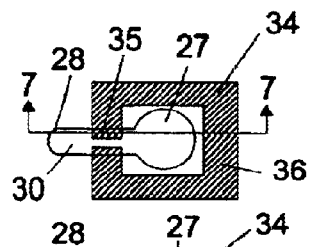
FIG. 6 is a view as in FIG. 4 with electrode conductors formed on the substrate.
Figure 7:
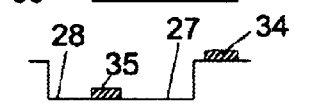
FIG. 7 is a cross-sectional view taken generally along the lines 7—7 of FIG. 6.
Figure 8:
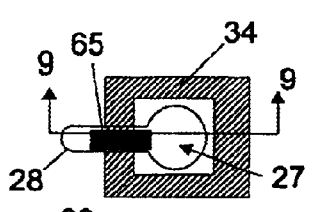
FIG. 8 is a view as in FIG. 6 showing the formation of a sacrificial layer in the channel in the substrate.
Figure 9:
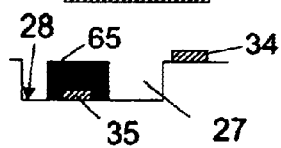
FIG. 9 is a cross-sectional view taken generally along the lines 9—9 of FIG. 8.
Figure 10:
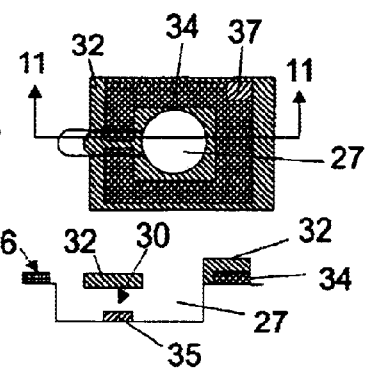
FIG. 10 is a view as in FIG. 8 showing the formation of an insulating layer over the electrode conductors and spanning the channel after removal of the sacrificial layer.
Figure 11:
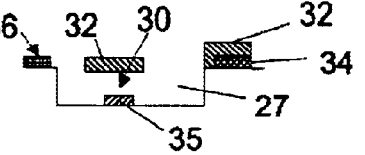
FIG. 11 is a cross-sectional view taken generally along the lines 11—11 of FIG. 10.

An exemplary process for fabricating the electrodes 23 and 24 is shown in FIGS. 4–11. The process is illustrated in these figures for the anode electrode 23, but it is understood that the same process may be utilized for forming the cathode electrode 24. As shown in FIG. 4 and the cross-sectional view of FIG. 5, a first mask is used to define the regions of the reservoir 27, terminal port 28 and channel 30 which are then recessed by etching to a suitable depth (e.g., 30 $\mu$m). Next, as illustrated in FIG. 6 and in the cross-sectional view of FIG. 7, a second mask is used to form a pattern for deposition of thin film electrode conductors 34, e.g., platinum. Then, as illustrated in FIG. 8 and the cross-sectional view of FIG. 9, a third mask is used to define a mold for a sacrificial layer 65, e.g., electroplated copper which may have a thickness selected to determine the depth of channel 30 below the surface, which allows selection of the flow rate. As shown in FIG. 10 and the cross-sectional view of FIG. 11, the final mask is used to define the insulating layer 27, e.g., polyimide, which extends over the channel 30 supported by the sacrificial layer 65. After the coating is formed, the sacrificial layer 65 (e.g., copper) is etched away, leaving the coating 32 extending over the channel 30 and over the sections 35 of the electrode conductors in the channel. A hydrophobic coating 66 is then preferably applied to the inter-electrode surface 55. The hydrophobic film 66 helps to eliminate electrophoresis of water that may otherwise occur during prolonged operation. Devices may be formed in this manner at relatively low cost and disposed of after use, if desired. The devices also can be readily cleaned and reused.

Figure 19:
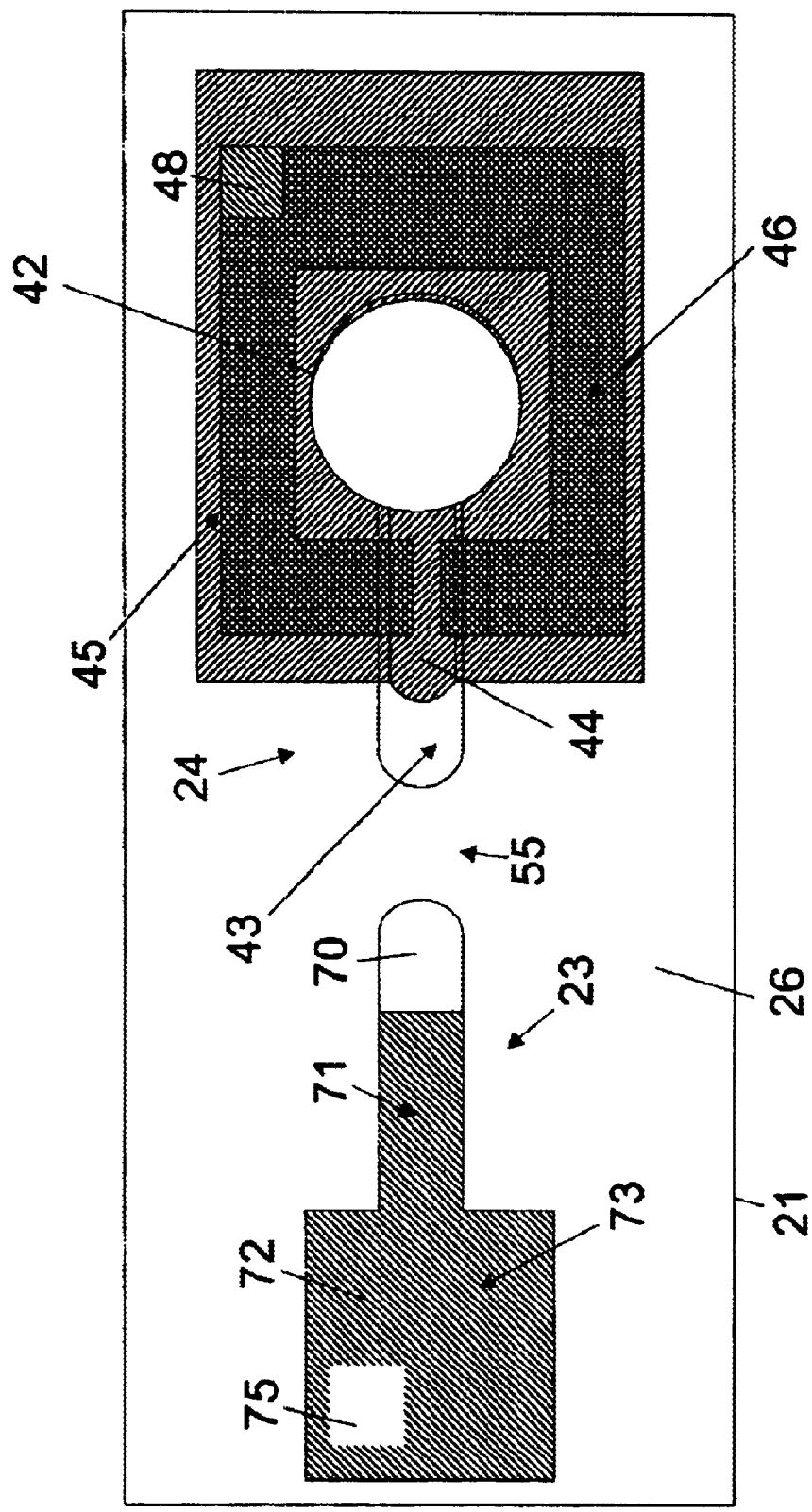
FIG. 19 is a plan view of glow discharge apparatus in accordance with the invention having a cathode liquid electrode and a metal anode electrode.
Figure 20:
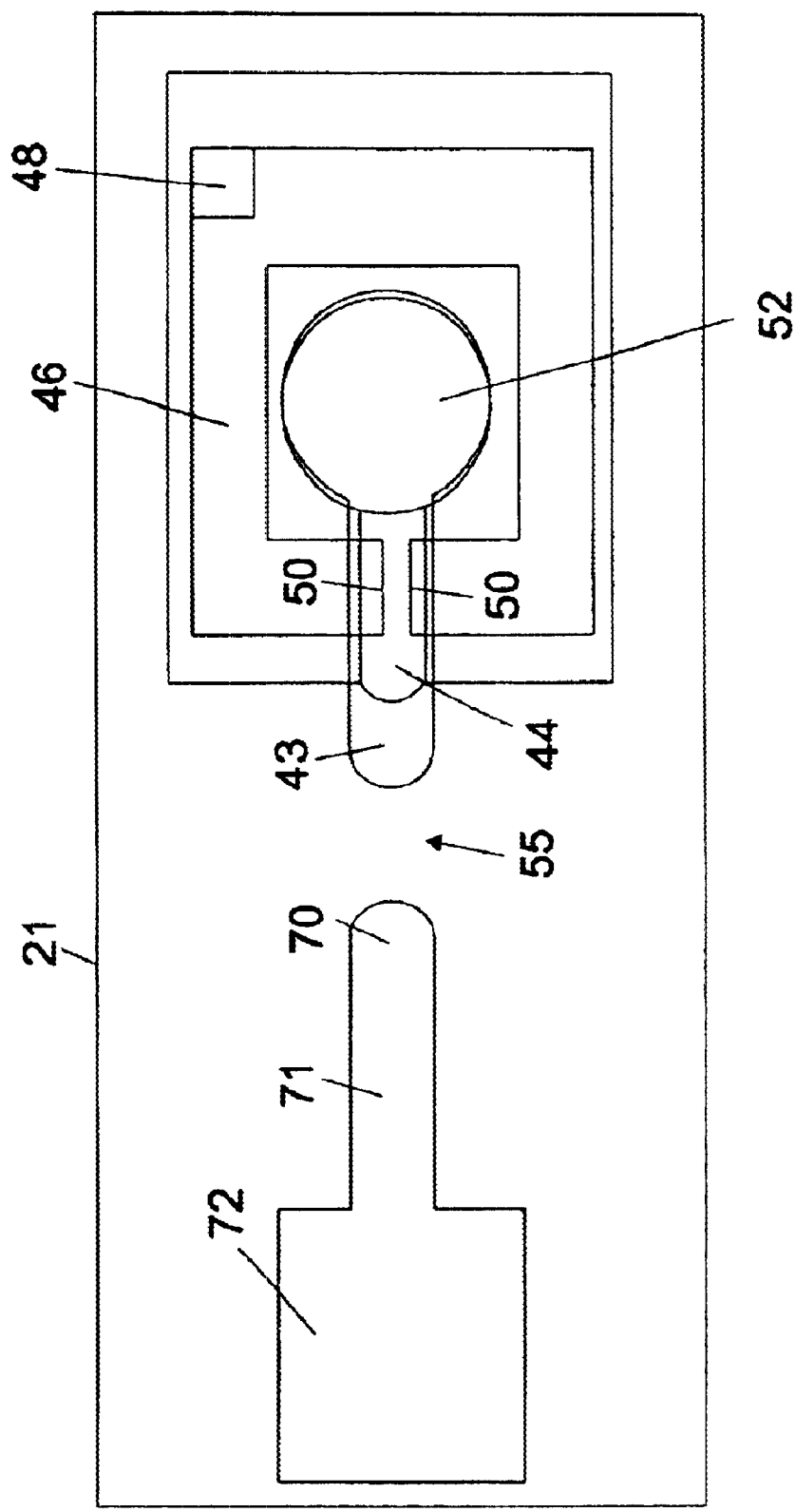
FIG. 20 is a plan view of the substrate with reservoir, channels and electrode conductors formed thereon for the apparatus of FIG. 19.

The present invention may also be embodied utilizing a solid anode electrode and a liquid cathode electrode, as illustrated in FIG. 19. The cathode electrode 24 is formed in the same manner as discussed above with respect to the apparatus of FIGS. 1 and 2. The anode electrode 23 is formed of an electrical conducting metal, e.g., copper, etc. deposited on the top surface 26 of the substrate as a unitary conductor with an exposed portion forming a terminal port 70 spaced from the cathode terminal port 43 by the inter-electrode gap 55, a conducting channel 71 which extends back to a pad 72, both of which are covered by an insulating material 73, e.g., polyimide, with an area 75 left open in the insulating layer to allow connection to the underlying anode electrode pad 72. FIG. 20 illustrates the substrate before the insulating layers are formed over the conductors for the cathode and anode electrodes.

The glow discharge apparatus of the invention may be enclosed within a chamber which can either be evacuated to pressure levels below atmospheric or charged to higher pressure levels, and the gases comprising the ambient atmosphere can also be selected as desired. It is a particular advantage of the present invention that it can be operated under vacuum pressures, as well as at atmospheric pressures. The apparatus of the invention develops a self-confined plasma the extent of which can be controlled by controlling the ambient pressure. By varying he ambient pressure, it is possible to control the electron temperature of the discharge, which allows the apparatus to be optimized for particular desired wavelengths of light. For example chemicals having spectral emissions at shorter wavelengths may have more sensitivity at lower pressures, which increases the electron temperature.

The following are examples of analyses conducted utilizing the exemplary apparatus as discussed above. It is understood that these examples are provided for purposes of illustrating the invention, but the invention is not limited thereto.

Figure 12:
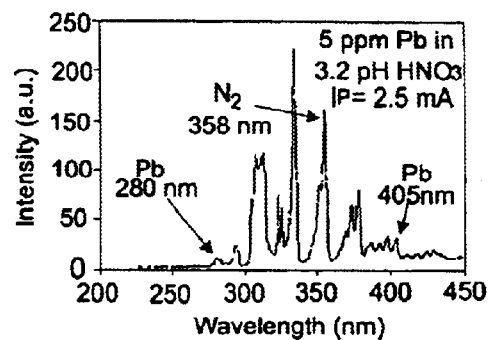
FIG. 12 is a spectrum taken with the apparatus of the invention from a sample containing 5 ppm Pb.
Figure 13:
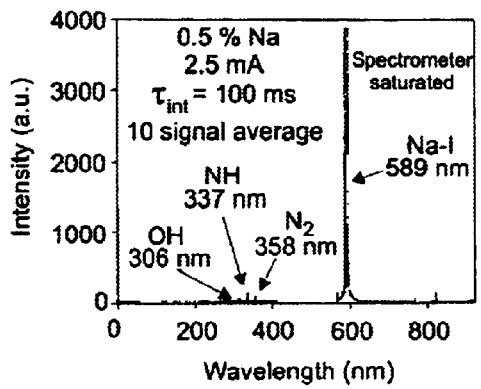
FIG. 13 is a spectrum taken with the apparatus of the invention of an NaCl sample with a concentration of 5,000 ppm.
Figure 14:
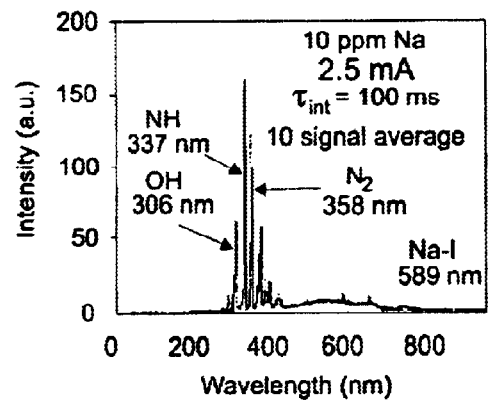
FIG. 14 is a spectrum taken with the apparatus of the invention of an NaCl sample with a concentration of 10 ppm.

FIG. 12 shows the typical spectral output of a sample containing 5 ppm Pb dissolved in nitric acid with a pH of 3.2. A discharge current of 2.5 mA was used. Two dominant spectral lines characteristic to Pb are seen at 280 nm and at 405 nm. The large spike at 358 nm is characteristic of $N_2$. The lead spectra are a result of the impurities sputtered from the liquid electrode, while the $N_2$ spectra which are seen in all discharges, are due to the air ambient. Spectra of saline solution at 10 ppm to 5000 ppm concentrations are shown in FIGS. 13 and 14. These show the primary Na contaminant line at 589 nm, as well as $N_2$. The NH and OH ionic lines are also visible as a result of the sputtered water and its reaction with the atmosphere. In FIG. 13, the case of 5000 ppm Na, the sodium spectral intensity is so strong that the spectrometer is saturated at the Na wavelength, and the signal is much stronger than the $N_2$ lines. In FIG. 14, the case of 10 ppm Na, the $N_2$ lines dominate the Na lines.

Figure 15:
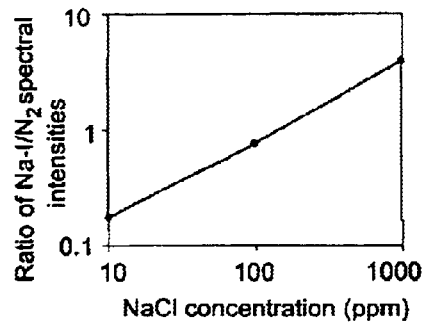
FIG. 15 is a graph illustrating the ratio of Na to $N_2$ spectral intensities as a function of NaCl concentration in spectra obtained with the apparatus of the invention.

By measuring the ratio of the spectral intensities of the primary contaminant to $N_2$, it is possible to determine the concentration of the impurity over a wide dynamic range. This is a valuable feature. FIG. 15 shows the averaged ratio of Na to $N_2$ spectra for Na concentration ranging from 10 ppm to 1000 ppm. The ratio of the spectral intensities varies by almost two orders of magnitude.

Figure 16:
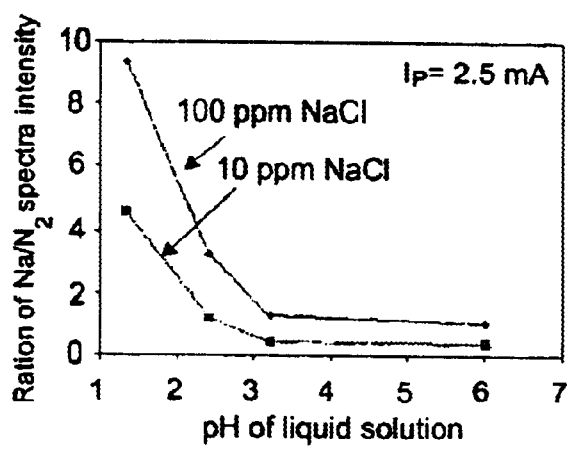
FIG. 16 are graphs showing the ratio of Na to $N_2$ spectral intensities as a function of pH of the tested solution in spectra obtained using the apparatus of the invention.
Figure 17:
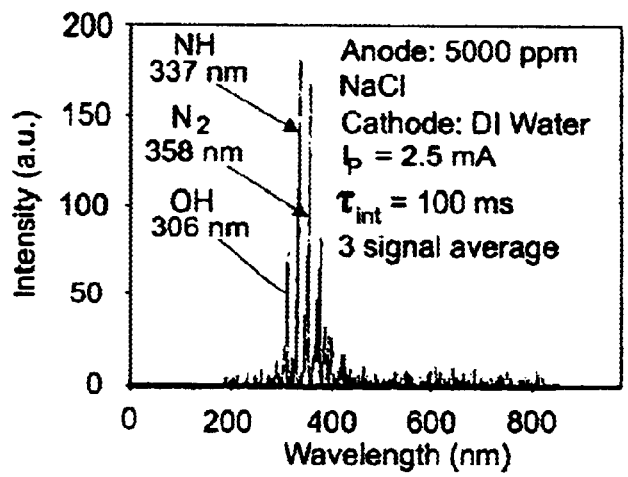
FIG. 17 is a spectrum taken with the apparatus of the invention in an experiment to confirm that the analytes measured are taken from the cathode liquid.

The intensity of the sodium line can be increased by modifying the pH of the sample under test with nitric acid, while the intensity of the nitrogen line remains relatively unchanged. This results in the ratio of the Na to $N_2$ spectral intensity lines increasing as the pH is decreased, which can be useful for extending the impurity detection limits, as illustrated in FIG. 16.

To determine the source of the impurity ions in the glow discharge, the cathode electrode of one device was filled with 5000 ppm NaCl, and the anode electrode with deionized (DI) water. This provided a spectrum similar to FIG. 13, indicating that positive gas ions from the discharge sputtered the cathode. The spectrum obtained under the reverse polarity did not show the Na line as shown in FIG. 15. This indicates that the dominant impurity delivery mechanism is sputtering from the cathode as opposed to fluid heating and vaporization. This is an important feature because it permits inorganic impurities which are nonvolatile to be introduced into the plasma. It eliminates the need for spraying the water into the plasma, which is the approach used in conventional devices.

Figure 18:
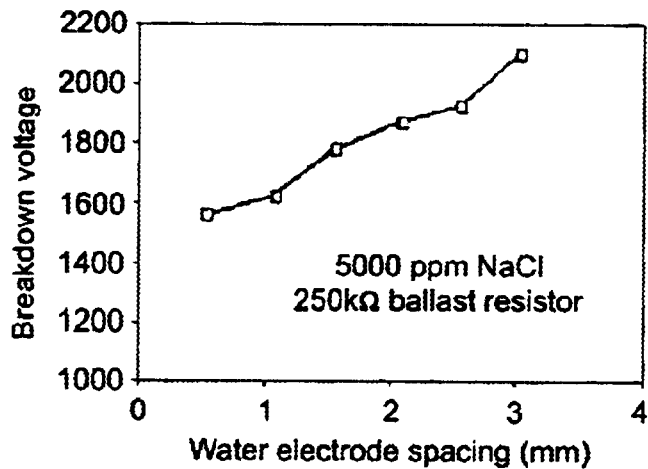
FIG. 18 is a graph illustrating breakdown voltage as a function of inter-electrode gap in the apparatus of the invention for a sample composed of 5,000 ppm NaCl.

The impact of varying the inter-electrode gap was tested using 5000 ppm NaCl on device variants, and the results are illustrated in FIG. 18. These results showed a linear relationship between this dimension and the breakdown voltage. The voltage drop within the water channel can be substantial, but lowering of the pH can reduce this. It is also possible to reduce the drive voltage by using a metal thin film electrode as the anode.

In addition to use in the detection of water impurities, the invention may be utilized as a light source with a customized spectrum. As an example, the apparatus of the invention was tested with a 10,000 ppm chromium solution in 5% nitric acid in the cathode reservoir. Chrome provides multiple dominant spectral lines in the 200–207 nm range. It was found that the emission spectral power of the ultraviolet (UV) range increases as the device is put under vacuum. This is believed to be due to the increased electron energy in discharges at lower operating pressures. A device operated at 100 Torr, with 16 mA current and 650 volts, was found to produce 8.3 mW of UV spectral power in the 195–235 nm wavelength range. This allows the device to be utilized for on-chip UV sources. Other constituents of the water in the cathode reservoir can be chosen to obtain emission at other wavelengths, including visible wavelengths.

It is understood that the invention is not confined to the embodiments set forth herein as illustrative, but embraces all such forms thereof as come within the scope of the following claims.

What is claimed is:

1. Glow discharge apparatus having a liquid microelectrode comprising:
   (a) a substrate having a top surface, a cathode electrode and an anode electrode formed thereon, the cathode electrode including a cathode terminal port formed as a depression in the substrate extending below the top surface of the substrate to hold a liquid therein, and the anode electrode including an anode terminal port formed as a depression in the substrate extending below the top surface of the substrate to hold a liquid therein, the anode terminal port spaced from the cathode terminal port by an inter-electrode gap, the substrate being electrically insulating between the anode electrode and cathode electrode; and
   (b) an anode electrical conductor on the substrate electrically connected to the anode electrode and a cathode electrical conductor on the substrate electrically connected to the cathode electrode.

2. The apparatus of claim 1 wherein the cathode electrode includes a cathode reservoir in the substrate and a cathode channel in the substrate extending from the cathode reservoir to the cathode terminal port, and wherein the anode electrode includes an anode reservoir in the substrate and an anode channel in the substrate extending from the anode reservoir to the anode terminal port.

3. The apparatus of claim 2 wherein the anode conductor extends from the anode channel on the top surface of the substrate to a position spaced away from the anode channel and the cathode conductor extends from the cathode channel on the top surface of the substrate to a position spaced away from the cathode channel, and including a layer of insulating material covering the cathode and anode conductors on the surface of the substrate with openings through the layer of insulator at which electrical leads may be connected to the anode conductor and the cathode conductor.

4. The apparatus of claim 3 wherein the anode conductor has two sections, each section extending into the anode channel and extending outwardly from the anode channel and around the anode reservoir to be joined together on the surface of the substrate, and wherein the cathode conductor comprises two sections extending outwardly from the cathode channel and around the cathode reservoir to be joined together on the surface of the substrate.

5. The apparatus of claim 4 wherein the cathode and anode conductors are formed of a conducting metal in a layer deposited on the surface of the substrate.

6. The apparatus of claim 2 further including an electrically insulating material extending over a portion of each of the anode channel and cathode channel to form a covered anode channel extending from the anode reservoir to the anode terminal port and a covered cathode channel extending from the cathode reservoir to the cathode terminal port.

7. The apparatus of claim 6 wherein the insulating material covering portions of the anode channel and cathode channel is polyimide.

8. The apparatus of claim 2 wherein the anode and cathode reservoirs, terminal ports and channels are formed as depressions in the substrate extending below the top surface of the substrate.

9. The apparatus of claim 8 wherein the reservoirs are formed as circular depressions in the substrate.

10. The apparatus of claim 1 wherein spacing of the inter-electrode gap between the anode terminal port and cathode terminal port is in the range of 0.5 mm to 10 mm.

11. The apparatus of claim 1 wherein the substrate is formed of glass.

12. The apparatus of claim 1 further including a DC power supply connected to the anode and cathode conductors to apply a DC voltage between the anode and cathode conductors.

13. The apparatus of claim 1 wherein the spacing of the inter-electrode gap between the anode terminal port and cathode terminal port is less than about 4 mm.

14. The apparatus of claim 1 further including an optical fiber extending from a position adjacent to the inter-electrode gap to a remote position, and a spectrometer connected to the optical fiber at the remote position such that the optical fiber directs light generated from the area of the inter-electrode gap to the spectrometer.

15. The apparatus of claim 1 further including a hydrophobic coating on an inter-electrode surface under the inter-electrode gap between the anode and cathode terminal ports.

16. The apparatus of claim 1 wherein the cathode terminal port and anode terminal port have dimensions less than 1,000 µm on a side.

17. Glow discharge apparatus having a liquid microelectrode comprising:
(a) a substrate having a top surface, a cathode reservoir and an anode reservoir formed therein, a cathode channel extending from the cathode reservoir to a cathode terminal port for holding a liquid therein and an anode channel extending from the anode reservoir to an anode terminal port for holding a liquid therein that is spaced from the cathode terminal port by an inter-electrode gap, the substrate being electrically insulating between the anode reservoir, channel and terminal port and the cathode reservoir, channel and terminal port; and
(b) an anode electrical conductor extending into the anode channel to make electrical contact with liquid held therein and a cathode electrical conductor extending into the cathode channel to make electrical contact with liquid held therein.

18. The apparatus of claim 17 wherein the anode conductor extends from the anode channel on the top surface of the substrate to a position spaced away from the anode channel and the cathode conductor extends from the cathode channel on the top surface of the substrate to a position spaced away from the cathode channel, and including a layer of insulating material covering the cathode and anode conductors on the surface of the substrate with openings through the layer of insulator at which electrical leads may be connected to the anode conductor and the cathode conductor.

19. The apparatus of claim 18 wherein the anode conductor has two sections, each section extending into the anode channel and extending outwardly from the anode channel and around the anode reservoir to be joined together on the surface of the substrate, and wherein the cathode conductor comprises two sections extending outwardly from the cathode channel and around the cathode reservoir to be joined together on the surface of the substrate.

20. The apparatus of claim 19 wherein the cathode and anode conductors are formed of a conducting metal in a layer deposited on the surface of the substrate.

21. The apparatus of claim 18 further including an electrically insulating material extending over a portion of each of the anode channel and cathode channel to form a covered anode channel extending from the anode reservoir to the anode terminal port and a covered cathode channel extending from the cathode reservoir to the cathode terminal port.

22. The apparatus of claim 21 wherein the insulating material covering portions of the anode channel and cathode channel is polyimide.

23. The apparatus of claim 17 wherein the anode and cathode reservoirs, terminal ports and channels are formed as depressions in the substrate extending below the top surface of the substrate.

24. The apparatus of claim 23 wherein the substrate is formed of glass.

25. The apparatus of claim 23 wherein the reservoirs are formed as circular depressions in the substrate.

26. The apparatus of claim 17 further including a DC power supply connected to the anode and cathode conductors to apply a DC voltage between the anode and cathode conductors.

27. The apparatus of claim 17 wherein the spacing of the inter-electrode gap between the anode terminal port and cathode terminal port is less than about 4 mm.

28. The apparatus of claim 17 further including an optical fiber extending from a position adjacent to the inter-electrode gap to a remote position, and a spectrometer connected to the optical fiber at the remote position such that the optical fiber directs light generated from the area of the inter-electrode gap to the spectrometer.

29. The apparatus of claim 17 further including a hydrophobic coating on an inter-electrode surface under the inter-electrode gap between the anode and cathode terminal ports.

30. The apparatus of claim 17 wherein the spacing of the inter-electrode gap between the anode terminal port and cathode terminal port is in the range of 0.5 mm to 10 mm.

31. The apparatus of claim 17 wherein the cathode terminal port and anode terminal port have dimensions less than 1,000 μm on a side.

32. Glow discharge apparatus having a liquid microelectrode comprising:

(a) a substrate, a cathode electrode and an anode electrode formed thereon, the cathode electrode including a cathode reservoir and a cathode channel extending from the cathode reservoir to a cathode terminal port for holding a liquid therein that is spaced from the anode electrode by an inter-electrode gap, the anode electrode and the cathode electrode being electrically insulated from each other; and (b) an anode electrical conductor electrically connected to the anode electrode and a cathode electrical conductor electrically connected to the cathode electrode.

33. The apparatus of claim 32 wherein the anode conductor extends from the anode electrode on a top surface of the substrate to a position spaced away from the anode electrode and the cathode conductor extends from the cathode electrode on the top surface of the substrate to a position spaced away from the cathode electrode, and including a layer of insulating material covering the cathode and anode conductors on the surface of the substrate with openings through the layer of insulator at which electrical leads may be connected to the anode conductor and the cathode conductor.

34. The apparatus of claim 33 wherein the cathode conductor comprises two sections extending outwardly from the cathode channel and around the reservoir to be joined together on the surface of the substrate.

35. The apparatus of claim 33 wherein the cathode and anode conductors are formed of a conducting metal in a layer deposited on the top surface of the substrate.

36. The apparatus of claim 33 further including an electrically insulating material extending over a portion of the cathode channel to form a covered cathode channel extending from the cathode reservoir to the cathode terminal port.

37. The apparatus of claim 36 wherein the insulating material covering portions of the cathode channel is polyimide.

38. The apparatus of claim 33 wherein the cathode reservoirs, terminal ports, and channels, are formed as depressions in the substrate extending below the top surface of the substrate.

39. The apparatus of claim 32 wherein the substrate is formed of glass.

40. The apparatus of claim 32 further including a DC power supply connected to the anode and cathode conductors to apply a DC voltage between the anode and cathode conductors.

41. The apparatus of claim 32 wherein the spacing of the inter-electrode gap between the anode electrode and cathode terminal port is less than about 4 mm.

42. The apparatus of claim 32 wherein the spacing of the inter-electrode gap between the anode electrode and cathode terminal port is in the range of 0.5 mm to 10 mm.

43. The apparatus of claim 32 further including an optical fiber extending from a position adjacent to the inter-electrode gap to a remote position, and a spectrometer connected to the optical fiber at the remote position such that the optical fiber directs light generated from the area of the inter-electrode gap to the spectrometer.

44. The apparatus of claim 32 further including a hydrophobic coating on an inter-electrode surface under the inter-electrode gap between the anode and cathode electrodes.

45. The apparatus of claim 32 wherein the anode electrode is formed as a conductive metal on a surface of the substrate having an exposed portion separated from the cathode electrode by the inter-electrode gap.

46. A method of generating glow discharges with a liquid microelectrode comprising:

(a) providing a substrate with a cathode electrode and an anode electrode formed thereon, the cathode electrode including a cathode terminal port that is spaced from the anode electrode by an inter-electrode gap, the anode electrode and the cathode electrode being electrically insulated from each other, and providing a liquid in the cathode terminal port; and (b) applying a voltage between the anode electrode and the cathode electrode sufficient to generate a glow discharge in the inter-electrode gap and to sputter liquid contained in the cathode terminal port into the glow discharge to excite the liquid and any constituents therein to provide light emissions indicative of the liquid and its constituents.

47. The method of claim 46 further including analyzing the light emitted from the glow discharge with a spectrometer to provide a spectrum of the glow discharge.

48. The method of claim 47 wherein the glow discharge is generated in air and further including comparing the spectral intensities in the spectrum obtained to the emission line for $N_2$ to determine the relative concentration of constituents with respect to $N_2$.

49. The method of claim 46 wherein the cathode electrode further includes a cathode reservoir and a cathode channel extending from the cathode reservoir to the cathode terminal port, and providing liquid to the cathode reservoir and flowing the liquid from the cathode reservoir through the cathode channel to the cathode terminal port to replenish liquid that is sputtered from the cathode terminal port.

50. The method of claim 46 wherein the anode electrode includes an anode terminal port, an anode reservoir, and a channel extending from the anode reservoir to the anode terminal port, and providing liquid to the anode reservoir and flowing the liquid through the channel to the anode terminal port, the anode terminal port being spaced from the cathode terminal port by the inter-electrode gap such that the glow discharge occurs between the liquid in the anode terminal port and the liquid in the cathode terminal port.

51. The method of claim 46 wherein the anode electrode includes an anode terminal port holding liquid therein and including the steps of applying a DC voltage in one polarity between the anode electrode and the cathode electrode while analyzing the light emitted from the glow discharge with a spectrometer to provide a spectrum of the glow discharge with liquid sputtered from the cathode terminal port, and then applying DC voltage in the opposite polarity between the anode electrode and cathode electrode while analyzing the light emitted from the glow discharge with liquid sputtered from the anode terminal port with a spectrometer to provide another spectrum.

* * * * *